United States Patent [19]
Kubotsu et al.

[11] Patent Number: 5,854,082
[45] Date of Patent: Dec. 29, 1998

[54] PROCESS FOR MEASURING COMPLEMENT ACTIVITY AND REAGENT USED THEREFOR

[75] Inventors: Kazuhisa Kubotsu; Sachiko Yamamoto; Masaaki Kida, all of Amagasaki, Japan

[73] Assignee: Wako Pure Chemical Industries, Ltd., Osaka, Japan

[21] Appl. No.: 756,363

[22] Filed: Nov. 26, 1996

Related U.S. Application Data

[63] Continuation of Ser. No. 300,318, Sep. 2, 1994, abandoned.

[30] Foreign Application Priority Data

Sep. 7, 1993 [JP] Japan ..................... 5-246332
Nov. 17, 1993 [JP] Japan ..................... 5-311229

[51] Int. Cl.[6] .................................................. G01N 33/53
[52] U.S. Cl. .................. 436/518; 436/528; 436/821; 436/829; 435/975; 530/387.1; 530/388.9; 530/389.1
[58] Field of Search .................. 435/4, 7.1, 7.9, 435/967, 968, 975; 436/518, 528, 17, 821, 829; 530/387.1, 388.9, 389.1

[56] References Cited

FOREIGN PATENT DOCUMENTS

| 0 382 400 A3 | 8/1990 | European Pat. Off. . |
| 62-163966 | 7/1987 | Japan . |
| 62-299764 | 12/1987 | Japan . |
| 63-293470 | 11/1988 | Japan . |
| 1-155271 | 6/1989 | Japan . |

OTHER PUBLICATIONS

Kinsky et al., *Complement–Dependent Damage to Liposomes Prepared from Pure and Forssman Hapten*, "Biochemistry" vol. 8, No. 10, pp. 4149–4158, (1969).

Geiger et al., *Immunochemical Determination of Ganglioside GM, By Inhibition of Complement–Dependent Liposome Lysis*, "Journal of Immunological Methods", 17, pp. 7–19, (1977).

Bowden et al., *Homogeneous, Liposome–Based Assay for Total Complement Activity in Serum*, "Clinical Chemistry", vol.32, No. 2, pp 275–278, (1986).

Derwent Publications Ltd., GB; JP A 01 155 271—Jun. 19, 1989, Abstract.

Patent Abstracts of Japan; Tomioka Kanji et al.; Jun. 7, 1994, JP A 6 160 390—Abstract.

Patent Abstracts of Japan; Kanegafuchi Chem Ind. Co. Ltd., Sep. 13, 1989, JP–A–01 229 970—Abstract.

Biochemica et Biophysica Acta; "Biomembranes", vol. 557, No. 1, Oct. 19, 1979 Amsterdam, pp. 9–23.

Masaki et al, J. Immurol. Methods, 123 (1):19–24 Sep. 29, 1989.

Paul et. "Fundamental Immunology", 1985 by Raven Press NY NY p. 680.

Sigma Chemical Company outa logue, 1992 p. 282–283.

Vance et al "The Biochemistry of Lipids and membranes", 1985 by Benjamin/Cummings Publishing Co Inc, Calfornina p. 36–39.

*Primary Examiner*—Patricia Duffy
*Attorney, Agent, or Firm*—Armstrong, Westerman, Hattori, McLeland & Naughton

[57] ABSTRACT

A reagent composition comprising (a) liposomes encapsulating a marker therein, immobilizing a hapten on liposome membranes and having a size in the range of 100 to 500 nm in terms of mean particle size plus twice the standard derivation, and (b) an antibody to the hapten is effective for measuring human complement activity easily and precisely with excellent storage stability.

8 Claims, 1 Drawing Sheet

PROCESS FOR MEASURING COMPLEMENT ACTIVITY AND REAGENT USED THEREFOR

This application is a continuation of application Ser. No. 08/300,318 filed Sep. 2, 1994, now abandoned.

BACKGROUND OF THE INVENTION

This invention relates to a process for measuring complement activity by quantitative analysis and a reagent composition used therefor.

The complement system is a collective term of about 20 kinds of proteins present in animal serum such as human serum. The complement system plays an important role for defending living bodies from invading foreign substances and bacteria by recognition and removal thereof. It is well known that the complement system has two pathways for activation, that is, the classical pathway wherein the activation is brought about by an immune complex and the alternative pathway wherein the activation is brought about by polysaccharides. In the classical pathway, the complement component is orderly activated one after another by an immune complex of a foreign substance (antigen) such as bacterium mainly, and an antibody to the antigen to finally destroy the foreign substance membrane, resulting in making the foreign substance die or lyse. The classical pathway includes, for example, a reaction wherein erythrocyte sensitized by hemolysin is led to hemolysis, and a reaction wherein liposome membrane sensitizing hapten thereon is destroyed as in the present invention. On the other hand, the alternative pathway does not require participation of an antibody. For example, in the alternative pathway, complement is activated by only a contact with a poly-saccharide, which is a component constituting cell walls of bacteria, or a virus. Recently, the measurement of activity of a complement system, that is, the measurement of a complement activity has been noticed as an index of diagnosis and therapy of active stage of systemic lupus erythematosus, rheumatoid arthritis, cryoglobulinemia-vasculitis, some forms of nephritis, and inherited deficiencies of the complement system etc.

As a process for measuring a complement activity now generally and widely used, it is known the Mayer method or its variations wherein hemolysis activity of complement is measured using antibody-sensitized sheep erythrocyte ["Rinsho Kensaho Teiyo", pp. 1233–1234, 29ed, 5th print, 1985 published by Kanehara Shuppan Co., Ltd.; J. Clin. Chem., 12, 143 (1983), etc.]. But the Mayer method is a very complicated method wherein a number of samples with various dilutions for one sample to be measured are prepared to carry out the reaction, and complement activity is measured by obtaining an amount for bringing about 50% hemolysis ($CH_{50}$ U/ml) based on such results. Further, there are various problems in that the erythrocytes used are poor in storage stability, sensitivity for complement is different depending on individual differences of animals, etc. Therefore, the Mayer method cannot be said as a preferable method.

On the other hand, it is reported various methods for measuring complement activity using liposomes which are more stable, less different between production lots, and prepared so as to be subjected to membrane damaging reaction by complement activity in place of erythrocytes (Japanese Patent Unexamined Publication (JP-A) Nos. 63-293470, 1-155271, 62-16396, 62-299764, etc.). But even in these methods using liposomes, there is a problem of sedimentation and aggregation of the liposomes during storage of reagent solutions dispersing the liposomes. Particularly, in the measurement using an autoanalyzer, such a phenomenon causes various problems. For example, since almost autoanalyzers are designed to have a cooling device for reagent solutions, which can be subjected to the measurement at any time while set in the autoanalyzer, when sedimentation and aggregation in the reagent solutions take place during the storage or the long-period measurement, the measurement is damaged due to variation of measuring sensitivity.

In order to solve such problems, it is proposed to use only liposomes immobilizing a specific functional group such as a pyridyl group in place of using the liposomes immobilizing an antibody thereon and an antigen to the antibody. But since such a method has a problem in that the reaction principle is different from the Mayer method wherein complement activity is measured based on the antigen-antibody reaction, this method is not preferable. Further, since these prior art measuring methods usually require the measurement at 37° C. for a reaction time of 1 hour, there is another problem in that the reaction time is too long to apply them to autoanalyzers.

Recently, the measurement using an autoanalyzer is particularly noticed and the measurement of human complement activity using an autoanalyzer is earnestly desired. But, since usual autoanalyzers are designed so as to conduct reactions for about 5 to 15 minutes, it is difficult to apply human complement activity measurement requiring a long period of reaction time to such auto-analyzers.

In addition, at the time of measuring human complement activity, calibration curves are usually prepared by using complement activity standard solutions, and the complement activity in samples are generally obtained by using the calibration curves. As the standard solutions for complement activity, there are generally used human serum and guinea pig serum. Since the human serum is difficult to obtain and difficult to control, commercially available reagents for the measurement often attaching guinea pig serum as standard solutions for complement activity. But, there is a difference between human complement and guinea pig complement in the reaction rate at the initial time of the reaction [J. Immunol. Methods, 17, 7–19 (1977)]. Therefore, when guinea pig complement is used as standard solutions for measuring human complement activity, since a long time is required for the measurement, there is a problem for applying said method to autoanalyzers.

Considering the above-mentioned problems, it has long been desired to develop methods for measuring human complement activity using liposomes stabler than erythrocytes derived from living bodies and less in difference between production lots, with simpler procedures and shorter time and being able to apply to autoanalyzers, and to develop reagent compositions for the measurements.

SUMMARY OF THE INVENTION

It is an object of the present invention to provide a process for measuring human complement activity excellent in dispersibility and standing storage stability, capable of measuring in a short time and applicable to autoanalyzers, and using liposomes, and a reagent composition used therefor.

The present invention provides a process for measuring human complement activity, which comprises
reacting a sample with liposomes having a size in the range of 100 to 500 nm, which range is within a mean particle size in nm plus twice the standard deviation, each value obtained from particle size distribution measured by a dynamic light scattering method, encapsulating a marker therein, and immobilizing a hapten on surfaces of liposome membranes, and an antibody to the hapten, measuring an amount of liberated marker according to the degree of rupture of liposome membranes, and measuring human complement activity in the sample on the basis of the amount of liberated marker thus obtained.

The present invention also provides a reagent composition for measuring human complement activity comprising (a) liposomes having a size in the range of 100 to 500 nm, which range is within a mean particle size in nm plus twice the standard deviation, each value obtained from particle size distribution measured by a dynamic light scattering method, encapsulating a marker therein, and immobilizing a hapten on surfaces of liposome membranes, and (b) an antibody to the hapten.

DESCRIPTION OF THE PREFERRED EMBODIMENTS

Figure 1:
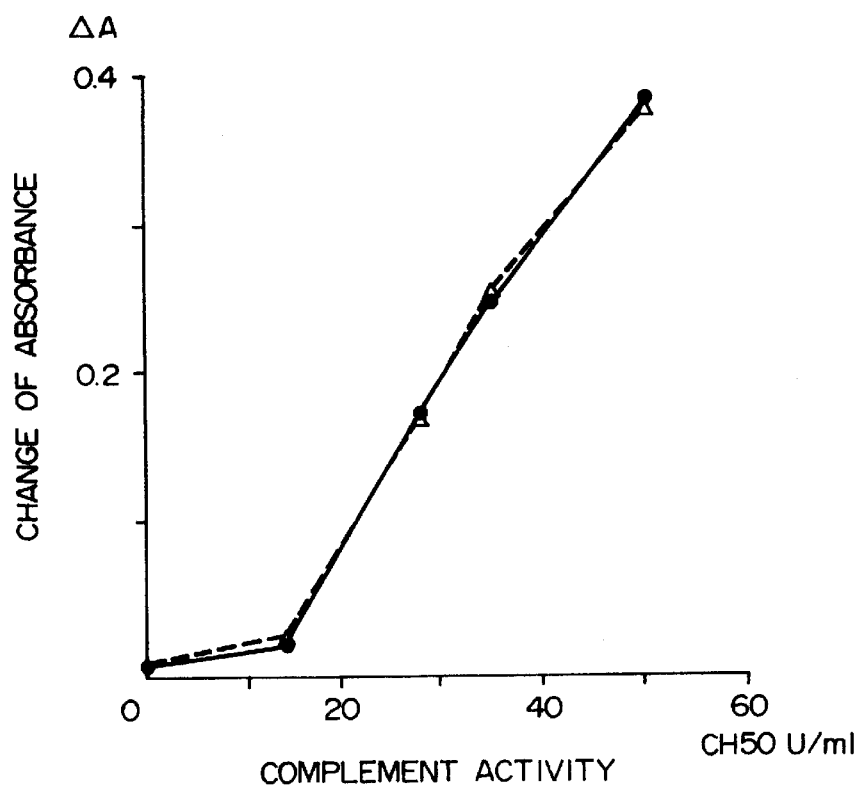
FIG. 1 is a calibration curve showing a relationship between complement activity ($CH_{50}$ U/ml) and a change of absorbances ($\Delta A$) at 340 nm obtained in Example 5.

The reagent solution for measuring human complement activity of the present invention prepared by using liposomes having a size in the range of 100 to 500 nm, which range is within a mean particle size in nm plus twice the standard deviation, each value obtained from particle size distribution measured by a dynamic light scattering method, encapsulating a marker therein, and immobilizing a hapten on surfaces of liposome membranes, does not cause sedimentation and aggregation during storage or at a time of measurement requiring a long period of time unlike known reagents, so that it is suitable for applying to autoanalyzers. Further, it was also found that the reaction rates of serum of rat, goat, or sheep are the same as that of human serum. Thus, it becomes possible to measure complement activity precisely in a short time of about 5 to 15 minutes when calibration curves are prepared using such serum in place of guinea pig serum conventionally used as standard solutions for measuring complement activity, since the reaction rate at the initial stage of the reaction is the same as that of human serum.

The liposomes usable in the present invention encapsulate a marker therein and immobilize a hapten on surfaces of liposome membranes. Further, the liposomes have a size in the range of 100 to 500 nm, preferably 150 to 350 nm, which range is within a mean particle size in nm plus twice the standard deviation, each value obtained from particle size distribution measured by a dynamic light scattering method [H. Terada, T. Yoshimura, ed." Manual for Liposome Experiments in Life Science", pp. 103–106, Suplinger Fairlark Tokyo, published Aug. 1, 1992, etc.]. Such liposomes can be prepared by conventional methods using conventional membrane constituting components.

For example, the liposomes can be prepared by conventional methods such as the vortexing method, the sonication method, the surfactant removal method, the reversed phase evaporation method (REV method), the ethanol injection method, the ether vaporization method, the pre-vesicle method, the French press extrusion method, the $Ca^{2+}$-induced method, the annealing method, the freeze-thawing method, the freeze-drying method, the W/O/W emulsion method, etc., and methods such as the stable plurilamellar vesicle method (SPLV method) reported by S. M. Gruner et al. [Biochemistry, 24, 2833 (1985)]. The thus prepared liposomes are passed through membranes having predetermined pore sizes using a French press, a pressed filter or an extruder to give liposomes having the objected property.

As the main constituent of membrane of the liposomes, there can be exemplified each a combinations of two or more of substances used as materials for membrane in preparation of conventional liposomes, i.e. natural lecithins (e.g. egg yolk lecithin, soybean lecithin, etc.); phospholipids such as dipalmitoylphosphatidylcholine DPPC), dimyristoylphosphatidylcholine (DMPC), distearylphosphatidylcholine (DSPC), dioleoylphosphatidylcholine (DOPC), dipalmitoylphosphatidylethanolamine (DPPE), dimyristoylphosphatidylethanolamine (DMPE), dipalmitoylphosphatidylglycerol (DPPG), dimyristoylphosphatidylglycerol (DMPG), dimyristoylphosphatidic acid (DMPA), egg yolk phosphatidylglycerol, etc.; glycolipids such as ganglioside glycolipid, sphingoglycolipid, glyceroglycolipid, etc.; and mixtures of these materials mentioned above and cholesterols. Needless to say, it is possible to use sheep erythrocytes-chloroform extraction fractions [S. C. Kinsky: Biochemistry, 8, 4149 (1969)] as a constituting component for liposomes.

As the marker encapsulated in the liposomes, there can be used those disclosed in D. Monroe; J. Liposome Res. 1(3), 339–377 (1989–90), for example, enzymes such as alkaline phosphatase, glucose-6-phosphate dehydrogenase, β-galactosidase, etc.; substrates for enzymes such as 4-methylumbelliferyl β-D-galactoside, p-hydroxyphenylpropionic acid, 4-methylumbelliferyl phosphate, glycose-6-phosphoric acid, etc.; substances which can emit fluorescence such as carboxyfluorescein, fluorescein isothiocyanate, fluorescein isocyanate, tetrarhodamine isothiocyanate, 5-dimethylamino-1-naphthalenesulfonyl chloride, etc.; dyes such as Arsenazo III, 4-(2-pyridylazo)resorcinol, 2-(5-bromo-2-pyridylazo)-5-(N-propyl-N-sulfopropylamino)phenol sodium salt, etc.; luminescent substances such as luminol, isoluminol, luciferin, eosin Y, auramine O, bis(2,4,6-trichlorophenyl) oxalate, N-methylacridinium ester, etc.; spin marker such as 2,2,6,6-tetramethylpiperidin-1-oxyl (TEMPO), etc. These markers can be used singly or as a mixture thereof.

As the marker, there can be used any one which can be detectable when liberated (released) from liposomes, membranes of which are ruptured by the action of complement against an antigen-antibody complex formed on the membranes of liposomes. The marker is selected depending on the detecting method, sensitivity and stability of liposomes. When an enzyme is encapsulated, since the sensitivity becomes higher due to amplification of reaction and detection can be carried out by usually measuring absorbances, the liposomes encapsulating an enzyme are more preferable for applying to autoanalyzers.

The amount of the marker encapsulated in the liposomes changes depending on the kind of marker and is not limited particularly, so long as a sufficient difference is shown when the liposome membrane is lysed. For example, in the case of using glucose-6-phosphate dehydrogenase as the marker, there is prepared an enzyme solution, which is used as a solution containing a marker at the time of preparation of liposome, in a concentration of usually 1000 to 5000 U/ml, preferably 2000 to 3000 U/ml.

As the hapten which is to be immobilized on the liposome membranes, there can be used those which can be immobilized on the liposome membranes and can react with an antibody to the hapten. Examples of the hapten are glycolipid antigens such as Forssman antigen, GM1, etc.; aromatic compounds such as dinitrobenzene, trinitrobenzene, etc.; hormones such as thyroxine, etc.; drugs such as theophylline, phenytoin, etc.

The hapten can be immobilized on the liposomes by conventional methods. For example, a phospholipid derivative which is combined with a glycolipid antigen or a hapten mentioned above can be used as a liposome membrane constituting component as described in S. C. Kinsky: Biochemistry 8, 4149 (1969), S. Shichijo: Journal of Immunological Methods, 85, 53–63 (1985), K. Uemura: Biochemistry, vol. 11, No. 22, 4085 (1972), T. Masaki: Journal of Immunological Methods, 123, 19–24 (1989), C. Braman: Bio. Technology, April, 349 (1984), U. Glagasigij; Chem. Pharm. Bull. 36, 1086 (1988), K. Kubotsu: Clin. Chem. 38, 808 (1992), etc. It is also possible to immobilize the hapten on surfaces of liposome membranes by the crosslinking method described in "Continued Biochemical Experiment Lecture 5: Immuno-Biochemical Experimental Method", 1st ed. edited by Chemical Society of Japan and Tokyo Kagaku Dojin, pp. 144–148 (1986).

As crosslinking agents usable in the crosslinking method, there can be used N-succinimidyl-3-(2-pyridyldithio) propionate (SPDP), N-succinimidyl 4-(p-maleimidophenyl) butylate (SMPB), N-succinimidyl 4-(p-maleimidophenyl) acetate (SMPA), N-succinimidyl 4-(p-maleimidophenyl) propionate acetate (SMPP), N-(4-maleimidobutylyloxy) succinimide (GMBS), N-(6-maleimidocaproyloxy) succinimide (EMCS), etc.

As the antibody, there can be used any antibodies which are against the hapten immobilized on the liposome membranes or which show cross reaction with the hapten. For example, there can be used either polyclonal antibodies prepared by immunizing animals such as horse, cattle, sheep, rabbit, goat, rat, mouse, etc. with a hapten which conjugates to albumin etc. according to a conventional method, for example, a method described in Tadashi Matsuhashi et al: "Meneki Jikkengaku Nyumon" 2nd. ed., Gakkai-Shuppan Center Ltd., 1981; or monoclonal antibodies produced by hybridomas obtained by fusing cells from a tumor live of mice together with mouse spleen cells previously immunized with a hapten which conjugates to albumin etc. according to a conventional method, for example, the cell fusion method established by G. Köhler and C. Milstein [Nature, 256, 495 (1975)]. These polyclonal and monoclonal antibodies can be used singly or as a mixture thereof. Further, these antibodies can be used in the form of included in serum or in ascites. If non-specific reaction at the time of measuring complement activity is wanted to inhibit, it is desirable to use these antibodies after purifying into IgG fractionation, etc. using ammonium sulfate fractionation, ion exchange chromatography, gel filtration chromatography, affinity chromatography, etc.

The measurement of human complement activity using the reagent composition mentioned above can be carried out as follows.

First, liposomes having a size in the range of 100 to 500 nm, which range is within a mean particle size in nm plus twice the standard deviation, each value obtained from particle size distribution measured by a dynamic light scattering method, encapsulating a marker therein, and immobilizing a hapten on surfaces of liposome membranes, are mixed with a sample (for example, human serum containing complement, etc.) in a suitable buffer solution and incubated usually at 20° to 50° C., preferably 25° to 40° C., usually for 3 to 60 minutes, preferably 5 to 30 minutes. As the buffer solution, there can be used phosphate buffer, borate buffer, tris(hydroxymethyl)aminomethane (Tris) buffer, Good's buffers, veronal buffer, etc. Such a buffer solution is preferably adjusted to have an osmotic pressure of usually 150 to 500 mOsm/kg, preferably 200 to 360 mOsm/kg and a pH of usually 5 to 9, preferably 6 to 8. To the resulting solution, an antibody to the hapten immobilized on the liposome membrane is added to carry out the reaction. After the reaction, the liberated (released) marker which becomes detectable is measured according to a conventional method depending on the marker used. The measured values are compared with, for example, calibration curves obtained by using suitable serum with known complement activity (e.g. human serum, rat serum, goat serum, sheep serum, guinea pig serum, etc.) as complement activity standard solutions in the same manner as mentioned above.

As the complement activity standard solutions, there can be used serum of suitable animals such as rat, goat, sheep, human being, guinea pig etc. Considering the commercial availability, to have a property similar to human complement, etc., it is preferable to use serum of rat, goat, sheep, etc. Among them, the rat serum is more preferable, since its property is most similar to the property of human serum.

The serum derived from these animals can of course be used by dissolving a freeze-dried product with water or a suitable solvent. Further, it is also possible to use these serum by diluting with a suitable solution, condensing by means of ultrafiltration, removing components which do not pertain to the complement reaction from the serum, and the like. If necessary, it is possible to add one or more sugars, proteins, antiseptics, stabilizers, buffers, etc. to the serum derived from animals.

The amount (concentration) of the liposomes used for measuring complement activity is usually 0.1 to 250 nmol/ml, preferably 1 to 50 nmol/ml in terms of the phospholipid amount contained in the liposomes in the final reaction solution.

Needless to say, in the above-mentioned reaction, there may be present in the solution at the time of reaction conventional reagents used in immunoassays using known liposomes, for example, one or more proteins such as bovine serum albumin, gelatin, etc., sugars, chelating agents, reducing agents, various antiseptics, reagents necessary for measuring markers (e.g. substrates for enzymes, etc.). These reagents can be present in concentrations usually used in conventional complement immunoassays.

Methods for measuring the amount of marker change depending on the kind of marker used. For example, when an enzyme is used as the marker, the marker can be measured according to the method, for example, described in T. Kitagawa, T. Nambara, A. Tsuji and E. Ishikawa: "Enzyme Immunoassay Methods", an extra issue No. 31 of Tanpakushitsu Kakusan Koso, pp. 51–63, Kyoritsu-Shuppan Ltd., published on Sep. 10, 1987. When a substance emitting fluorescence is used as the marker, the measurement can be carried out, for example, as described in A. Kawano: "Zusetsu Keiko-kotai" 1st, ed. Soft Science, Inc., 1983. When a luminescent substance is used as the marker, the measurement can be carried out, for example, as described in T. Kitagawa, T. Nanbara, A. Tsuji and E. Ishikawa:

"Enzyme Immunoassay Methods", an extra issue No. 31 of Tanpakushitsu Kakusan Koso, pp. 252–263, Kyoritsu-Shuppan Ltd., published on Sep. 10, 1987. When a spin marker is used as the marker, the measurement can be carried out, for example, as described in T. Kitagawa, T. Nambara, A. Tsuji and E. Ishikawa: "Enzyme Immunoassay Methods", an extra issue No. 31 of Tanpakushitsu Kakusan Koso, pp. 264–271, Kyoritsu-Shuppan Ltd., published on Sep. 10, 1987. When a dye is used as the marker, the measurement can be carried out by measuring a maximum absorption wavelength of the dye using a spectrophotometer.

As the unit of human complement activity, $CH_{50}$ value (U/ml) is used in the Mayer method. But the unit is not limit to the $CH_{50}$ value.

The process of the present invention is suitable for the measurement using an autoanalyzer, but can also be applied to a manual method. Since the reagent solution containing liposomes has good storage stability, the complement activity can be measured easily and precisely. The combination of reagents used for the manual method or autoanalyzer is not particularly limited and can be selected optionally depending on circumstances of the autoanalyzer used and other factors. Considering storage stability, it is preferable to store the liposomes and the antibody to the hapten immobilized on the liposome membranes in different containers separately until the reaction time.

The reagent composition for measuring complement activity comprises (a) liposomes having a size in the range of 100 to 500 nm, which range is within a mean particle size in nm plus twice the standard deviation, each value obtained from particle size distribution measured by a dynamic light scattering method, encapsulating a marker therein, and immobilizing a hapten on surfaces of liposome membranes, and (b) an antibody to the hapten. The reagent composition may further contain a buffer solution for diluting the liposome and the antibody. Further, when an enzyme is used as the marker, a substrate for the enzyme can also be included as a component. In addition, the reagent composition may further contain as a complement standard solution a suitable animal serum such as serum derived from human being, rat, goat or sheep.

The present invention is illustrated by way of the following Examples.

EXAMPLE 1

Comparison of stability of liposomes having different (mean+2SD) values
(1) Preparation of liposomes immobilizing dinitrophenyl groups on liposome membranes and having different (mean+2SD) values [Dinitrophenyl immobilized liposomes]

Liposomes encapsulating glucose 6-phosphate dehydrogenase (G6PDH) and immobilizing dinitrophenyl groups on liposome membranes were prepared according to the vortexing method described in H. Terada and T. Yoshimura: "Liposome Experimental Manual in Life Science" P. 60–89, Suplinger Fairlark Tokyo Co., Ltd. 1992 as follows.

After dissolving 142 μmol of dimyristoylphosphatidylcholine (DMPC), 16 μmol of dimyristoylphosphatidylglycerol (DMPG), 164 μmol of cholesterol and 1.6 μmol of phosphatidylethanolamine derivative of dinitrobenzene (mfd. by Avanti Co., Ltd.) in 10 ml of chloroform, the resulting solution was dried under reduced pressure. To this, 15 ml of G6PDH aqueous solution [2500 U/ml in 10 mM tris(hydroxymethyl)aminomethane (Tris)/HCl buffer solution (pH 7.8)] was added and mixed using a vortex mixer. The thus obtained lipid hydration solution was equally divided into six, each being subjected to adjustment of particle size through membranes having suitable pore sizes. The resulting 6 kinds of liposome suspensions were transferred to centrifugation tubes, respectively. After removing the enzyme not encapsulated in the liposomes by centrifuging at 36000 rpm at 4° C., the resulting liposomes were suspended in 100 mM Tris/HCl buffer solution (pH 7.8) to give dinitrophenyl immobilized liposomes having different particle sizes.

Mean particle sizes, etc. of these liposomes were measured by the particle size analysis system (LPA-3000/3100, Otsuka Electronics, Co., Ltd.) using the dynamic light scattering method to give mean particle sizes (mean), the standard deviation (SD), each values obtained from individual particle size distribution, and the value of (mean+2SD) as shown in Table 1.

TABLE 1

| Liposome No. | Mean particle size (mean) | Standard deviation (SD) | mean + 2SD |
| --- | --- | --- | --- |
| 1 | 140 nm | 17 nm | 174 nm |
| 2 | 208 | 28 | 264 |
| 3 | 240 | 114 | 468 |
| 4 | 197 | 159 | 515 |
| 5 | 282 | 318 | 918 |
| 6 | 457 | 272 | 1001 |

(2) Standing storage stability of liposomes having different (mean+2SD) values

Six kinds of G6PDH encapsulating dinitrophenyl immobilized liposomes having different (mean+2SD) values prepared in above (1) were diluted with a gelatin-veronal buffer solution (hereinafter referred to as "GVB$^{++}$", see S. Inai, et al: "Hotai-gaku" Ishiyaku Shuppan K.K. 1983, etc.) and stored for predetermined periods by standing at 10° C., followed by sampling of 250 μl of supernatant. To this, 10 μl of human serum containing complement was added, and incubated at 37° C. for 5 minutes. Then, 125 μl of GVB$^{++}$ (pH 7.4) containing a sufficient amount of anti-dinitrophenyl antibody (goat, mfd. by ICN Co., Ltd., after purifying into IgG fractionation by ammonium sulfate fractionation and DEAE cellulose column chromatography), 24 mM of glucose 6-phosphoric acid (G6P) and 9 mM nicotinamide adenine dinucleotide (NAD) was added and reacted at 37° C. for 5 minutes. Then, the activation value of G6PDH was measured as a change of absorbance (ΔA) at 340 nm per minute.

The results are shown in Table 2.

TABLE 2

| | | ΔA after standing for predetermined period | | |
| --- | --- | --- | --- | --- |
| Liposome No. | mean + 2SD | Immediately after preparation | 24 hrs. | 1 week |
| 1 | 174 nm | 0.151 | 0.152 | 0.151 |
| 2 | 264 nm | 0.254 | 0.253 | 0.254 |
| 3 | 468 nm | 0.284 | 0.283 | 0.281 |
| 4 | 515 nm | 0.291 | 0.288 | 0.262 |
| 5 | 918 nm | 0.324 | 0.310 | 0.271 |
| 6 | 1001 nm | 0.362 | 0.340 | 0.245 |

As is clear from the results of Table 2, when liposomes having the (mean+2SD) value of 500 nm or less are used (Liposome Nos. 1 to 3), no change of ΔA (change of absorbance) is admitted even after standing for 1 week. But when liposomes having the (mean+2SD) value of over 500 nm are used (Liposome Nos. 4 to 6), ΔA is gradually lowered. In other words, the liposomes having the mean+ 2SD) value of 500 nm or less are good in standing storage stability in the solution, but the liposomes having the (mean+2SD) value of over 500 nm are poor in standing storage stability in the solution.

When the solutions containing liposomes (Liposome Nos. 4 to 6) having the (mean+2SD) value of over 500 nm after stored without disturbing for 1 week were mixed sufficiently, and ΔA was obtained using the same reagents and the procedure as mentioned above. The obtained ΔA was the same as that immediately after the preparation.

From these results, it seems that liposomes are gradually precipitated or aggregated from the liposome solutions during storage without disturbance.

Further, when individual liposome undiluted solutions (lipid concentration 3000 nmol/ml) were stored for one month in a standing state, sedimentation of liposomes was admitted in the liposome undiluted solutions having the (mean+2SD) value of over 500 nm, while no sedimentation was admitted in the liposome undiluted solutions having the (mean+2SD) value of 500 nm or less.

EXAMPLE 2

Stability of liposome solutions was examined in the case of storing liposomes immobilized with a hapten or protein antigen on the membrane thereof and an anti-body to the hapten (or antigen) separately without disturbing until the measurement of complement activity, and in the case of storing them previously in the same solution without disturbing.

(1) Preparation of liposomes immobilizing a hapten on the membranes thereof (hapten immobilized liposomes)

Liposomes immobilized with dinitrophenyl groups as a hapten were prepared in the same manner and using the same reagents as in Example 1 (1). The adjustment of particle size was carried out by passing through a membrane having a pore size of 0.2 μm.

The resulting hapten immobilized liposomes were subjected to measurement by the particle size analysis system (LPA-3000/3100, mfd. by Otsuka Electronics, Co., Ltd.) using the dynamic light scattering method to give the following data derived from particle size distribution.

Mean particle size (mean): 165 nm

Standard deviation (SD): 39 nm (mean+2SD) value: 243 nm (2) Preparation of antibody-hapten complex immobilized liposomes The hapten immobilized liposomes prepared in above (1) and a sufficient amount of anti-dinitrophenyl antibody (goat, mfd. by ICN Co., Ltd.; after purifying into IgG fractionation by ammonium sulfate fractionation and DEAE cellulose column chromatography) were mixed and reacted at room temperature for 24 hours. After transferring to centrifugation tubes, the antibody not reacted to hapten on liposome membranes were removed by centrifuging at 36000 rpm at 4° C. Then, the resulting liposomes were suspended in 100 mM Tris/HCl buffer solution (pH 7.8) to give antibody-hapten complex immobilized liposomes.

(3) Preparation of protein antigen immobilized liposomes on membranes thereof (protein antigen immobilized liposomes)

① Preparation of SH group immobilized liposomes

After dissolving 71 μmol of dimyristoylphosphatidylcholine, 8 μmol of dimyristoylphosphatidyl glycerol, 82 μmol of cholesterol, and 2.0 μmol of phosphatidylethanolamine derivative of N-hydroxysuccinimidyl-3-(2-pyridyldithio) propionate (SPDP) in 5 ml of chloroform, the resulting solution was dried under reduced pressure. To this, 7.5 ml of G6PDH aqueous solution [2500 U/ml in 10 mM Tris/HCl buffer solution (pH 7.8)] was added and mixed to prepare liposomes. The resulting liposome suspension was passed through a membrane having a pore size of 0.2 μm to adjust the particle size. After transferring to a centrifugation tube, the enzyme not encapsulated in the liposomes was removed by centrifugation at 36,000 rpm at 4° C. After suspending in 100 mM Tris buffer solution (pH 7.8), SH group-containing liposomes (SH group immobilized liposomes) were obtained.

The resulting SH group immobilized liposomes were subjected to measurement of the particle size analysis system (LPA-3000/3100, mfd. by Otsuka Electronics, Co., Ltd.) using the dynamic light scattering method to give the following data derived from particle size distribution.

Mean particle size (mean): 204 nm

Standard Deviation (SD): 23 nm (mean+2SD): 250 nm

② Preparation of Protein antigen immobilized liposomes

To 1 ml of a solution of 2.0 mg/ml C reactive protein (CRP) subjected to previously dialysis with 0.01 M N-2-hydroxyethylpiperadine-N'-ethane sulfonic acid (HEPES) buffer solution (pH 4.5), 0.3% ethanol solution of SPDP was added to make 0.1 mM and reacted at room temperature with occasional stirring for 30 minutes. Then, the reaction solution was purified with Sephadex G-25 column to give SPDP modified CRP. To the SPDP modified CRP, dithiothreitol (DTT) was added to make about 50 mM, followed by reaction at room temperature for 30 minutes. After purifying with Sephadex G-25 column, thiol modified CRP was obtained. The thiol modified CRP and the SH group immobilized liposomes obtained in above were mixed and reacted at 4° C. overnight with gentle shaking. After removing unreacted CRP by centrifugation at 4° C. and 36,000 rpm, protein antigen immobilized liposomes were obtained.

The resulting protein antigen immobilized liposomes, were subjected to measurement by the particle size analysis system (LPA-3000/3100, mfd. by Otsuka Electronics, Co., Ltd.) using the dynamic light scattering method to give the following data derived from particle size distribution.

Mean particle size (mean): 2952 nm

Standard deviation (SD): 1210 nm (mean+2SD) value: 5372 nm (4) Preparation of antibody-protein antigen complex immobilized liposomes The protein antigen immobilized liposomes prepared in above (3) were mixed with a sufficient amount of anti-CRP antibody (rabit, mfd. by Nippon Biotest Labolatories, Ltd.; purified into lgG fractionation using ammonium sulfate fractionation and DEAE cellulose column chromatography), followed by reaction at room temperature for 24 hours. After transferring to centrifugation tube, antibody not immobilized on the liposome membranes was removed by centrifugation at 4° C. and 36,000 rpm. The resulting liposomes were suspended in 100 mM Tris/HCl buffer solution (pH 7.8) to give antibody-protein antigen complex immobilized liposomes.

(5) Storage stability of Liposomes

Individual liposomes prepared in above (1), (2), (3) and (4) were diluted with 100 mM Tris/HCl buffer solution (pH 7.8, containing 0.85% NaCl) so as to the lipid concentration 5 nmol/ml, respectively. After storing at 10° C. for predetermined period without disturbing, the mean particle size (mean) derived from particle distribution was measured using the particle size analysis system (LPA-3000/3100, mfd. by Otsuka Electronics, Co., Ltd.) applying the dynamic light scattering method. At the same time, deposition of liposomes was observed by the naked eye. Further the zeta-potential of each liposome after stored for 24 hours without disturbing was measured by laser dopular method with a laser electronics zeta-potential analyzer (LEZA-600, mfd. by Otsuka Electronics, Co., Ltd.).

The results are shown in Table 3.

For comparison, changes of the mean particle size and the like immediately after mixing of the hapten immobilized liposomes obtained in above (1) with anti-dinitrophenyl antibody were also measured and listed in Table 3.

TABLE 3

| Liposome No. | Mean particle size after standing (nm) | | | | | Zeta-potential (mV) |
|---|---|---|---|---|---|---|
| | Immediately after preparation | 1 hr | 3 hrs | 6 hrs | 24 hrs | |
| 1 | 200 | 196 | 197 | 193 | 198 | −17.0 |
| 2 | 685 | 1978 | 4363 | — | — | −5.2 |
| 3 | 4098 | — | — | — | — | −5.0 |
| 4 | 208 | 210 | 212 | 211 | 218 | −16.8 |
| 5 | 2197 | — | — | — | — | −8.9 |
| 6 | 3430 | — | — | — | — | −4.6 |

Note)
Liposome No. 1: hapten immobilized liposomes
Liposome No. 2: hapten immobilized liposomes + antibody
Liposome No. 3: antibody-hapten complex immobilized liposomes
Liposome No. 4: SH group immobilized liposomes
Liposome No. 5: protein antigen immobilized liposomes
Liposome No. 6: antibody-protein antigen complex immobilized liposomes
The mark "—": Aggregation of liposomes was observed by the naked eye.

As is clear from the results of Table 3, the liposomes having the (mean+2SD) value of 500 nm or less such as the hapten immobilized liposomes (Liposome No. 1) and the SH group immobilized liposomes (Liposome No. 4) show almost no change after storing without disturbing.

In contrast, when the hapten immobilized liposomes and anti-dinitrophenyl antibody are stored together without disturbing (Liposome No. 2), there is a tendency to enlarge the mean particle size with the lapse of time, that is, to enlarge the (mean 30 2SD) value. Further, aggregation of the liposomes was admitted when stored for 6 hours. Once aggregation was admitted, the liposome solution also showed aggregation of liposomes after several hours from sufficient stirring.

Further, in the case of the antibody-hapten complex immobilized liposomes (Liposome No. 3), the protein antigen immobilized liposomes (liposome No. 5) and the antibody-protein antigen complex immobilized liposomes (Liposome No. 6), the (mean+2SD) values were remarkably larger than those of the hapten immobilized liposomes (Liposome No. 1) and the SH group immobilized liposomes (Liposome No. 4), and aggregation was admitted after storing for 1 hour without disturbing.

In addition, the zeta-potential of the antibody-hapten complex immobilized liposomes, the protein antigen immobilized liposomes and the antibody-protein antigen complex immobilized liposomes is decreased compared with those of the hapten immobilized liposomes and the SH group immobilized liposomes.

Considering the above results, when protein is immobilized on liposome membranes by the antigen-antibody reaction, covalent bond, etc., sedimentation and aggregation easily take place due to lowering in the zeta-potential, etc. to lower the dispersibility and storage stability.

Therefore, it is desirable to store the hapten immobilized liposomes and the antibody to the hapten separately in different containers until the reaction for measuring complement activity.

EXAMPLE 3

Influences of (mean+2SD) value on complement activity measurement
(Liposome solution)

A liposome solution prepared in the same manner as described in Example 1 (1) and using the same reagents as in Example 1 (1) was passed through membranes having a pore size of 0.2 μm, 0.4 μm or 0.6 μm, followed by dilution with 50 mM Tris/HCl buffer solution (pH 7.8, containing 0.85% NaCl) so as to make the final lipid concentration 5 nmol/ml to give a liposome solution.
(Procedure)

The liposome in an amount of 250 μl was mixed with 10 μl of rat complement solution (complement activity: 33 $CH_{50}$ U/ml) and incubated at 37° C. for 5 minutes. To the resulting solution, 125 μl of 50 mM Tris/HCl buffer solution [pH 7.8, containing a sufficient amount of anti-dinitrophenyl antibody (goat, mfd. by ICN Co., Ltd.: purified into IgG fractionation by ammonium sulfate fractionation and DEAE cellulose column chromatography), substrate for enzyme (24 mM glucose 6-phosphate (G6P), 9 mM nicotinamide adenine dinucleotide (NAD)) and 0.85% NaCl] was added and reacted at 37° C. for 5 minutes. Then, an activation value was measured as a change of absorbance ($\Delta A_1$) at 340 nm per minute.

On the other hand, 250 μl of the liposome solution was mixed with 10 μl of a physiological saline solution in place of 10 μl of rat complement solution and incubated at 37° C. for 5 minutes. To the resulting solution, 125 μl of 50 mM Tris/HCl buffer solution [pH 7.8, containing a sufficient amount of anti-dinitrophenyl antibody (goat, mfd. by ICN Co., Ltd.:, purified into IgG fractionation by ammonium sulfate fractionation and DEAE cellulose column chromatography), substrate for enzyme (24 mM glucose 6-phosphate (G6P), 9 mM nicotinamide adenine dinucleotide (NAD)), 0.85% NaCl and a surfactant (digitonin 0.2%)] was added and reacted at 37° C. for 5 minutes to liberate G6PDH completely from the liposomes. The activation value of liberated G6PDH was measured as a change 0f absorbance ($\Delta A_2$) at 340 nm per minute. The amounts of encapsulated enzymes for individual liposomes having various (mean+2SD) values were obtained.

These results are shown in Table 4.

TABLE 4

| (mean + 2SD) value (nm) | $\Delta A_1$ | $\Delta A_2$ | $\Delta A_1/\Delta A_2 \times 100$ (%) |
|---|---|---|---|
| 254 | 0.18 | 0.23 | 78 |
| 275 | 0.22 | 0.27 | 81 |
| 240 | 0.28 | 0.35 | 80 |
| 468 | 0.30 | 0.38 | 79 |
| 474 | 0.31 | 0.40 | 77 |
| 420 | 0.31 | 0.42 | 74 |
| 662 | 0.35 | 0.54 | 65 |
| 1063 | 0.33 | 0.49 | 67 |
| 1019 | 0.36 | 0.56 | 64 |

As is clear from the results of Table 4, the liposomes having the (mean+2SD) value of 500 nm or less have larger values of $\Delta A_1/\Delta A_2 \times 100$. In other words, the detectable by the reaction with complement is large, and this means that the reactivity with complement is high.

EXAMPLE 4

(1) Comparison of liposome membrane lysis activity between human complement and various animal complement To 10 μl of human serum having a known complement activity (35 $CH_{50}$ U/ml), 250 μl of $GVB^{++}$ containing the DNP immobilized liposomes encapsulating G6PDH prepared in Example 1 (1) (Liposome No. 2) was added. After reacting at 37° C. for 5 minutes, 125 μl of $GVB^{++}$ adjusted to pH 7.4 and containing a sufficient amount of goat anti-DNP antibody and substrate for enzyme [24 mM glucose 6-phosphate (G6P), 9 mM nicotinamide adenine dinucleotide (NAD)] was added to the resulting solution, followed by reaction at 37° C. for 5 minutes. The activity value of G6PDH liberated from the liposomes by the 10 liposome membrane lysis (destruction) action by complement was measured as a change of absorbance (ΔA) at 340 nm per minute using NADH.

Then, fresh serums of rat, goat, sheep, guinea pig, mouse, rabit, and hamster in place of the fresh human serum were subjected to the same procedure as mentioned above to measure the change of absorbance (ΔA).

The results are shown in Table 5.

TABLE 5

| Kind of serums | Change of absorbance (ΔA) |
| --- | --- |
| Human serum (35$CH_{50}$ U/ml) | 0.20 |
| Rat serum | 0.34 |
| Goat serum | 0.45 |
| Sheep serum | 0.31 |
| Guinea pig serum | 0.04 |
| Mouse serum | 0.01 |
| Rabit serum | 0.01 |
| Hamster serum | 0.01 |

As is clear from the results of Table 5, the serums of rat, goat and sheep show the lysis activity equal to or more than the liposome membrane lysis activity of human serum (complement activity 35 $CH_{50}$ U/ml).

When the serums of rat, goat and sheep were diluted with a physiological saline solution so as to show the change of absorbance (ΔA) corresponding to the human serum complement activity of 30 $CH_{50}$ U/ml and the reaction with the lapse of time was measured under the same conditions as mentioned above, the results were in good agreement with the case of human serum.

(2) Relation between reaction time and liposome membrane lysis activity

To 10 μl of each serum of human being, rat, goat, sheep, and guinea pig, 250 μl of $GVB^{++}$ containing DNP immobilized liposomes encapsulating G6PDH and prepared in Example 1 (1) (Liposome No. 2) was added. Further 125 μl of $GVB^{++}$ containing a sufficient amount of goat anti-DNP antibody was added to the resulting each solution, and reacted at 37° C. for 5, 10, 30, 60 and 90 minutes. At each reaction time, 125 μl of $GVB^{++}$ adjusted to pH 7.4 and containing substrate for enzyme (24 mM G6P, 9 mM NAD) was added and reacted at 37° C. for 5 minutes, respectively.

The activity value of G6PDH liberated from liposomes by the liposome membrane lysis action of complement was measured as a change of absorbance (ΔA) at 340 nm per minute using NADH.

The results are shown in Table 6.

TABLE 6

| | Change of absorbance (ΔA) | | | | |
| --- | --- | --- | --- | --- | --- |
| Kind of serums | 5 min | 10 min | 30 min | 60 min | 90 min |
| Human serum (35$CH_{50}$ U/ml) | 0.15 | 0.15 | 0.15 | 0.15 | 0.15 |
| Rat serum | 0.26 | 0.26 | 0.26 | 0.26 | 0.26 |

TABLE 6-continued

| | Change of absorbance (ΔA) | | | | |
| --- | --- | --- | --- | --- | --- |
| Kind of serums | 5 min | 10 min | 30 min | 60 min | 90 min |
| Goat serum | 0.34 | 0.34 | 0.34 | 0.34 | 0.34 |
| Sheep serum | 0.23 | 0.23 | 0.23 | 0.23 | 0.23 |
| Guinea pig serum | 0.03 | 0.04 | 0.08 | 0.08 | 0.08 |

As is clear from the results of Table 6, the change of absorbance of the serums of human being, rat, goat and sheep becomes constant after 5 minutes due to almost completion of the reaction. On the other hand, in the case of guinea pig serum, it takes about 30 minutes to make the change of absorbance constant and to complete the reaction.

As is clear from the above results, since the reaction is completed in a short time as in human serum in the case of serums of rat, goat and sheep, it is possible to use the serums of rat, goat and sheep as a complement standard solution at the time of measuring human complement activity.

EXAMPLE 5

Measurement of human complement activity using dinitrophenyl immobilized liposomes (1) Preparation of dinitrophenyl immobilized liposome solution Liposomes prepared in the same manner as described in Example 1 (1) and using the same reagents as used in Example 1 (1) were passed a membrane having a pore size of 0.2 μl to adjust a particle size, and diluted with 50 mM Tris/HCl buffer solution (pH 7.8, containing 0.85% NaCl) so as to make the lipid concentration 5 nmol/ml.

The resulting dinitrophenyl immobilized liposome solution was subjected to measurement by the particle size analysis system (LPA-300/3100, mfd. by Otsuka Electronics, Co., Ltd.) using the dynamic light scattering method to give the following data derived from particle size distribution:

Mean particle size (mean): 165 nm

Standard deviation (SD): 39 nm (mean+2SD) value: 243 nm (2) Preparation of calibration curve and measurement of unknown complement activity of human serum Rat serum with known complement activity in an amount of 10 μl and 250 μl of dinitrophenyl immobilized liposome solution were mixed and incubated at 37° C. for 5 minutes. To the resulting solution, 125 μl of 50 mM Tris/HCl buffer solution [pH 7.8, containing a sufficient amount of anti-dinitrophenyl antibody (goat, mfd. by ICN Co., Ltd.; purified into IgG fractionation by ammonium sulfate fractionation and DEAE cellulose column chromatography), substrate for enzyme (24 mM G6P, 9 mM NAD) and 0.85% of NaCl] was added and reacted at 37° C. for 5 minutes. Then, activation value of G6PDH was measured as a change of absorbance (ΔA) at 340 nm per minute.

In FIG. 1, a calibration curve showing a relationship between complement activity ($CH_{50}$ U/ml) and ΔA is shown by -•-.

On the other hand, after storing the dinitrophenyl immobilized liposome solution at 10° C. for 1 week without disturbing, the supernatant was sampled to prepare a calibration curve showing a relationship between complement activity and ΔA using the supernatant in the same manner as mentioned above. The resulting calibration curve is shown by ---Δ--- in FIG. 1.

As is clear from FIG. 1, the two calibration curves are almost agreed. In other words, this means that the storage stability without disturbing of the dinitrophenyl immobilized liposome solution is remarkably good.

When unknown complement activity of human serum was measured in the same manner as mentioned above using the same reagents, the meaned value was in good agreement with that obtained by a conventional method (according to standard procedures using commercially available kits for measuring complement activity ($CH_{50}$) based on the principle of method 1/2.5).

The results are shown in Table 7.

TABLE 7

| Sample No. | Conventional method ($CH_{50}$ U/ml) | The present invention ($CH_{50}$ U/ml) |
|---|---|---|
| 1 | 19.8 | 18.6 |
| 2 | 32.1 | 31.5 |
| 3 | 37.0 | 38.1 |
| 4 | 37.0 | 36.3 |
| 5 | 28.6 | 27.4 |
| 6 | 30.8 | 31.6 |
| 7 | 25.6 | 24.8 |
| 8 | 34.8 | 35.2 |
| 9 | 29.2 | 30.1 |
| 10 | 42.6 | 43.0 |
| 11 | 29.9 | 29.6 |
| 12 | 41.7 | 41.7 |
| 13 | 41.0 | 41.0 |
| 14 | 30.5 | 30.0 |
| 15 | 39.1 | 39.4 |

EXAMPLE 6

Measurement of complement activity of human serum using phenytoin immobilized liposome solution (1) Preparation of phenytoin immobilized liposome solution Liposomes were prepared in the same manner as described in Example 1 (1) using the same reagents as used in Example 1 (1) except for using 1.6 μmol of phosphatidylethanolamine derivative of phenytoin [synthesized according to the process described in K. Kubotsu, et al.: Clin. Chem. 38 (6), pp. 808–812, 1992] in place of the phosphatidylethanolamine derivative of dinitrobenzene. The resulting liposomes were passed through a membrane having a pore size of 0.2 μm for adjusting the particle size, followed by dilution with 50 mM Tris/HCl buffer solution (pH 7.8, containing 0.85% NaCl) so as to make the lipid concentration 5 nmol/ml.

The resulting phenytoin immobilized liposomes were subjected to measurement by the particle size analysis system [LPA-3000/3100, mfd. by Otsuka Electronics, Co., Ltd.) using the dynamic light scattering method to give the following data derived from particle size distribution:

Mean particle size (mean): 177 nm

Standard Deviation (SD): 38 nm (mean+2SD) value: 253 nm (2) Preparation of calibration curve and measurement of unknown complement activity of human serum Goat serum with known complement activity in an amount of 10 μl and 250 μl of the phenytoin immobilized liposome solution were mixed and incubated at 37° C. for 5 minutes. To the resulting solution, 125 μl of 50 mM Tris/HCl buffer solution [pH 7.8, containing a sufficient amount of anti-phenytoin antibody (rabit, mfd. by Chemicon Co., Ltd.: purified into IgG fractionation by ammonium sulfate fractionation and DEAE cellulose column chromatography), substrate for enzyme (24 mM G6P, 9 mM NAD) and 0.85% NaCl] was added and reacted at 37° C. for 5 minutes. Then, activation value of G6PDH was measured as a change of absorbance ($\Delta A$) at 340 nm per minute.

Figure 2:
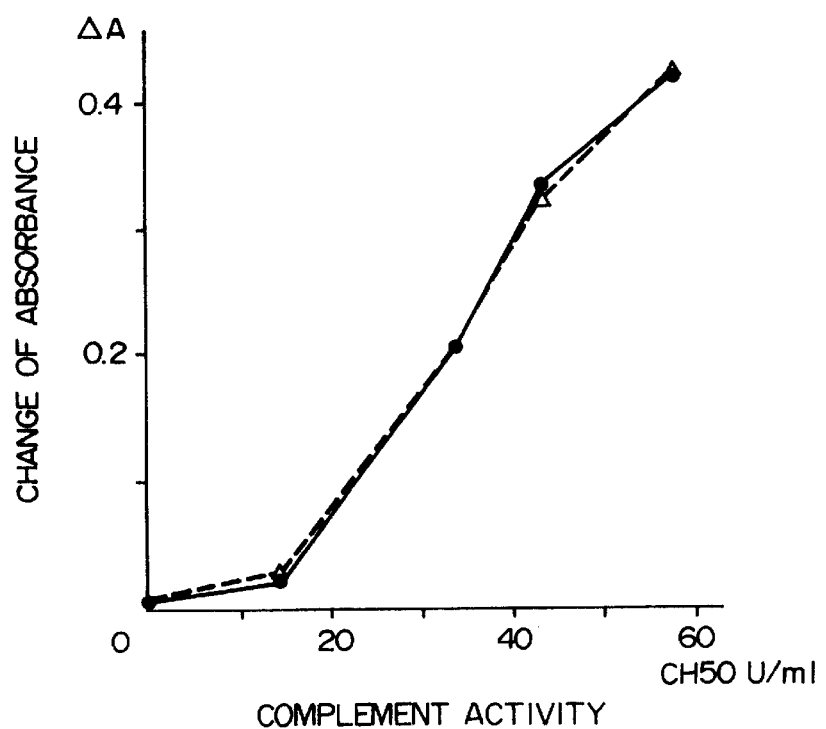
FIG. 2 is a calibration curve showing a relationship between complement activity ($CH_{50}$ U/ml) and a change of absorbances ($\Delta A$) at 340 nm obtained in Example 6.

In FIG. 2, a calibration curve showing a relationship between complement activity ($CH_{50}$ U/ml) and $\Delta A$ is shown by -•-.

On the other hand, after storing the phenytoin immobilized liposome solution at 10° C. for 1 week without disturbing, the supernatant was sampled to prepare a calibration curve showing a relationship between complement activity and $\Delta A$ using the supernatant in the same manner as mentioned above. The resulting calibration curve is shown by ---Δ--- in FIG. 2.

As is clear from FIG. 2, the two calibration curves are almost agreed. In other words, this means that the storage stability without disturbing of the phenytoin immobilized liposome solution is remarkably good.

When unknown complement activity of human serum was measured in the same manner as mentioned above using the same reagents, the measured value was in good agreement with that obtained by a conventional method (according to standard procedures using commercially available kits for measuring complement activity ($CH_{50}$) based on the principle of Mayer method 1/2.5).

The results are shown in Table 8.

TABLE 8

| Sample No. | Conventional method ($CH_{50}$ U/ml) | The present invention ($CH_{50}$ U/ml) |
|---|---|---|
| 1 | 35.3 | 34.9 |
| 2 | 34.7 | 33.7 |
| 3 | 36.3 | 37.2 |
| 4 | 27.3 | 27.9 |
| 5 | 25.0 | 25.9 |
| 6 | 28.1 | 28.6 |
| 7 | 29.0 | 28.7 |
| 8 | 28.0 | 27.8 |
| 9 | 28.7 | 28.7 |
| 10 | 35.4 | 35.2 |
| 11 | 19.2 | 20.0 |
| 12 | 14.4 | 14.1 |
| 13 | 30.4 | 30.1 |
| 14 | 35.4 | 35.7 |
| 15 | 26.4 | 27.4 |

As mentioned above, the present invention provides the reagent composition and the process for measuring complement activity easily in a short time with high measuring sensitivity and also excellent in standing storage stability compared with conventional methods. By applying the present invention, measurement of complement activity using liposomes can be carried out using an autoanalyzer with high precision and good reproductivity.

What is claimed is:

1. A reagent composition for measuring human complement activity consisting essentially of:

(a) liposomes having a size within the range of 100 to 500 nm, wherein the size is determined by a mean particle size in nm plus twice the standard deviation, said mean particle size and said standard deviation being obtained and calculated from a particle size distribution measured by a dynamic light scattering method, an encapsulated marker therein which is liberated and measured when the liposomes are ruptured by the action of a complement against an antigen-antibody complex formed on membranes of the liposomes, and a hapten immobilized on surfaces of liposome membranes which can react with an antibody to said hapten; and (b) an unbound antibody which reacts with said hapten immobilized on the surface of the liposome;

wherein said liposomes and said antibody are stored in different containers.

2. A reagent composition for measuring human complement activity consisting essentially of:

(a) liposomes having a size within the range of 100 to 500 nm, wherein the size is determined by a mean particle size in nm plus twice the standard deviation, said mean particle size and said standard deviation being obtained and calculated from a particle size distribution measured by a dynamic light scattering method, an encapsulated marker therein which is liberated and measured when the liposomes are ruptured by the action of a complement against an antigen-antibody complex formed on membranes of the liposomes, and a hapten immobilized on surfaces of liposome membranes which can react with an antibody to said hapten;

(b) an un-bound antibody which reacts with said hapten immobilized on the surface of the liposome; wherein said liposomes and said antibody are stored in difference containers; and (c) a serum derived from an animal as a complement standard solution.

3. A composition according to claim 2, wherein the complement standard solution is a serum derived from rat, goat, sheep or human being.

4. A composition according to claim 2, wherein the complement standard solution is a serum derived from rat.

5. A storage stable reagent composition for measuring human complement activity comprising:

(a) liposomes having a size within the range of 100 to 500 nm, wherein the size is determined by a mean particle size in nm plus twice the standard deviation, said mean particle size and said standard deviation being obtained and calculated from a particle size distribution measured, by a dynamic light scattering method, a marker encapsulated therein which is liberated and measured when the liposomes are ruptured by the action of a complement against an antigen-antibody complex formed on membranes of the liposomes, and a hapten immobilized on surfaces of liposome membranes which is capable of reacting with an antibody to said hapten; and (b) an un-bound antibody which reacts with said hapten immobilized on the surface of the liposome;

wherein said liposomes and said antibody are stored in different containers.

6. A composition according to claim 5, which further comprises (c) a serum derived from an animal as a complement standard solution.

7. A composition according to claim 6, wherein the complement standard solution is a serum derived from a rat, goat, sheep or human being.

8. A composition according to claim 7, wherein the complement standard solution is a serum derived from a rat.

* * * * *